Figure 1:
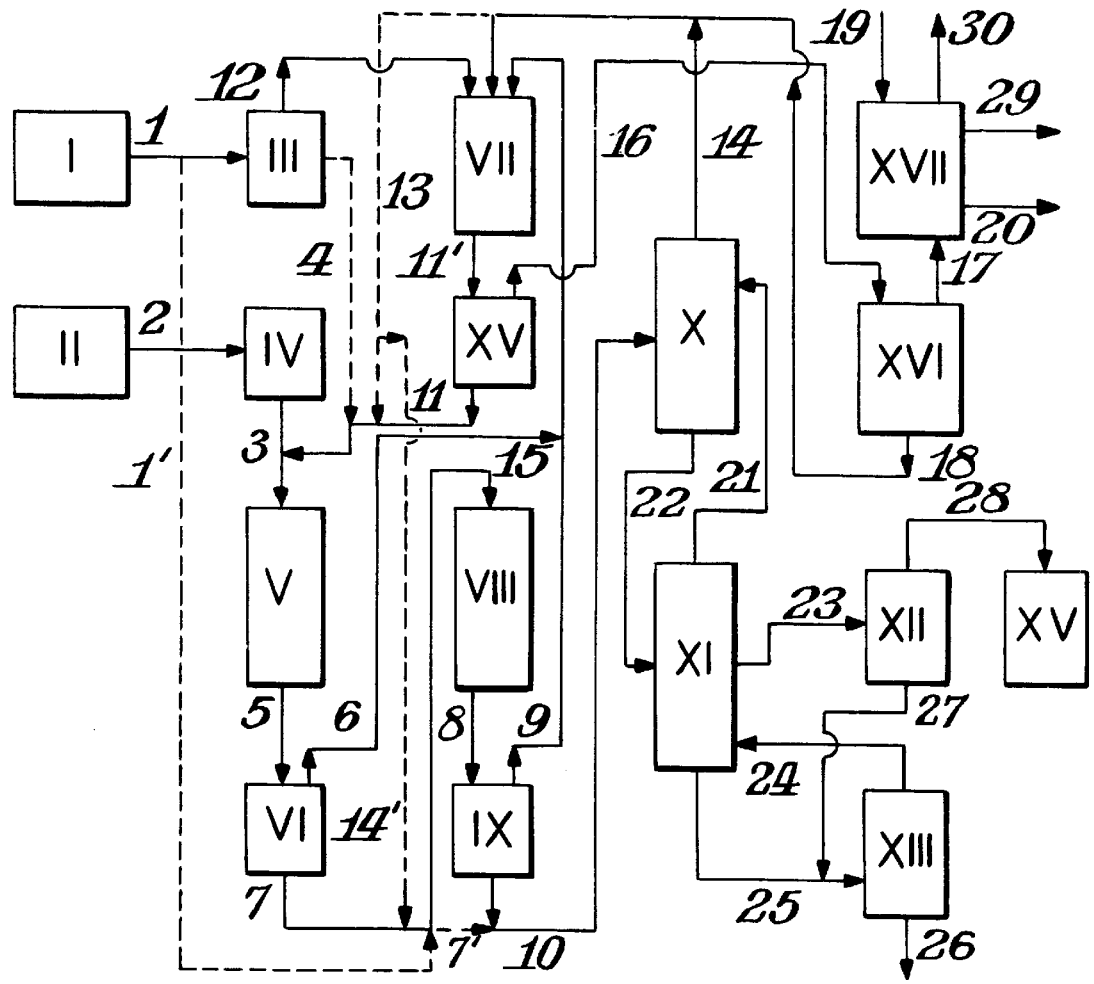

United States Patent [19]
Ooms et al.

[11] Patent Number: 5,900,501
[45] Date of Patent: * May 4, 1999

[54] PROCESS FOR THE CONTINUOUS PRODUCTION OF ARYL CARBONATES

[75] Inventors: Pieter Ooms; Hans-Josef Buysch, both of Krefeld; Steffen Kühling, Meerbusch; Gottfried Zaby, Leverkusen, all of Germany

[73] Assignee: Bayer Aktiengesellschaft, Germany

[*] Notice: This patent is subject to a terminal disclaimer.

[21] Appl. No.: 08/799,299

[22] Filed: Feb. 13, 1997

[30] Foreign Application Priority Data

Feb. 21, 1996 [DE] Germany .................. 196 06 384

[51] Int. Cl.⁶ ............................................. C07C 68/02
[52] U.S. Cl. .................. 558/274; 558/271; 558/272; 558/273

[58] Field of Search ...................... 558/271, 272, 558/273, 274

[56] References Cited

U.S. PATENT DOCUMENTS 5,710,310  1/1998  Ooms et al. ..................... 558/274

FOREIGN PATENT DOCUMENTS 0 757 029 A1  5/1997  European Pat. Off. .

*Primary Examiner*—Michael G Ambrose
*Attorney, Agent, or Firm*—Connolly & Hutz

[57] ABSTRACT

The present invention relates to a process for the continuous production of carbonates having aromatic ester groups by the reaction of aromatic hydroxy compounds with phosgene in the presence of heterogeneous catalysts, phosgene still present being removed from the stream of waste gas by returning the waste gas to an additional reactor.

1 Claim, 1 Drawing Sheet

| | |
|---|---|
| I | Storage tank for phenol |
| II | Storage tank for phosgene |
| III/IV | Heat exchangers |
| V, VII, VIII | Reactors |
| VI, IX, XV | Degasifiers |
| X, XI, XII, XIII | Distillation columns |
| XIV | Product container (DPC) |
| XVI | Cryogenic trap |
| XVII | HCl absorber |

PROCESS FOR THE CONTINUOUS PRODUCTION OF ARYL CARBONATES

The present invention relates to a process for the continuous production of carbonates having aromatic ester groups by the reaction of aromatic hydroxy compounds with phosgene in the presence of heterogeneous catalysts, phosgene still present being removed from the stream of waste gas by returning the waste gas to a secondary reactor.

It is known that aryl carbonates can be obtained by phase interface phosgenation (Schotten-Baumann reaction) of aromatic hydroxy compounds. The use of solvents and sodium hydroxide solution has an adverse effect here, as owing to the aqueous lye a partial saponification of phosgene or chloroformic esters can take place, large amounts of common salt are obtained as a secondary product and the solvent has to be recovered.

Proposals for processes without solvent are found in, for example, U.S. Pat. Nos. 2,837,555; 3,234,263; 2,362,865. But soluble catalysts are used, the separation of which from the products is elaborate.

It therefore appeared useful to employ heterogeneous, insoluble catalysts, which would considerably facilitate the working-up of the reaction mixture. There have also been proposals regarding this. Thus in EP-A 516 355 primarily aluminium trifluoride is recommended, optionally applied to supports such as aluminosilicates. The synthesis of aluminium fluoride is very elaborate and expensive, however, owing to the handling of fluorine or hydrofluoric acid. In WO 91/06526, metal salts on porous supports are also described as catalysts for the reactions according to the invention. A fully continuous phosgenation of phenol is possible on such catalysts only in the gas phase, but this involves relatively high reaction temperatures and the risk of decomposition of the labile chloroformic esters. A phosgenation of phenol in the liquid phase using these catalysts is obviously not feasible, as the hot, liquid phenol washes out the active catalyst components.

To date there has thus been no practicable proposal for a continuous procedure for the production of diaryl carbonates by phosgenation of aromatic hydroxy compounds in the presence of heterogeneous catalysts.

Such a process has now been found. It is characterised in that 1) a mixture of an aromatic hydroxy compound and optionally chloroformic ester thereof together with phosgene are passed into a reactor filled with heterogeneous catalyst and reacted therein in such a way that the heat of reaction is dissipated by evaporation of the educts and products and thus the reaction temperature rises by 50° C. at most above the inlet temperature of the reaction mixture, 2) the product leaving the reactor is degassed, the waste gas together with a molten stream of the aromatic hydroxy compound, which optionally contains some chloroformic ester, is passed into an additional waste gas reactor filled with heterogeneous catalyst and is reacted therein so that phosgene and optionally chloroformic ester are removed from the stream of waste gas, 3) the reaction product removed from the reactor and degassed is-either led away directly for working up or is fed into a second reactor, wherein residual chloroformic ester is reacted further, over heterogeneous catalyst, with aromatic hydroxy compound still present or introduced, to form diaryl carbonate, 4) the product leaving the second reactor is again degassed and this waste gas is passed into the waste gas reactor referred to in 2) with molten aromatic hydroxy compound, 5) the degassed product from the second reactor is fed into a distillation column, aromatic hydroxy compound and traces of chloroformic ester possibly still present are distilled off at the top and are reintroduced into the waste gas reactor or into the first reactor, 6) the bottoms of this first column are passed into a second distillation column, traces of low-boiling components possibly still present are removed from the diaryl carbonate at the top and are reintroduced into the upper part of the first column, 7) diaryl carbonate, possibly containing traces of high-boiling components, is removed from the gas space of the second column, 8) this product is passed into a third column and, by separating the residual quantities of high-boiling components as bottoms, pure diphenyl carbonate is obtained as overhead product, 9) the combined bottoms of the second and third column are passed into a fourth distillation unit, diaryl carbonate is distilled off at the top, is returned to the second column and the high-boiling components are removed from the bottom of the fourth distillation unit.

Aromatic hydroxy compounds for the process according to the invention are those corresponding to the formula

wherein

Ar signifies phenyl, naphthyl, anthryl, phenanthryl, indanyl, tetrahydronaphthyl or the group of a 5-membered or 6-membered aromatic heterocyclic compound having 1 or 2 hetero atoms selected from the group comprising N, 0 and S, wherein these isocyclic or heterocyclic groups may be substituted by one or more substituents such as straight chain or branched $C_1$–$C_4$ alkyl groups, $C_1$–$C_4$ alkenyl groups, $C_1$–$C_4$ alkoxy groups, phenyl groups or nitrile and halogen functions, and wherein the heterocyclic groups may also be fused to a benzene nucleus.

Examples of aromatic hydroxy compounds according to the invention are: phenol, o-, m- and p-cresol, o-, m- and p-isopropylphenol, the corresponding halophenols or alkoxyphenols, such as p-chlorophenol or p-methoxyphenol, furthermore monohydroxy compounds of naphthalene, anthracene and phenanthrene and additionally 4-hydroxypyridine and hydroxyquinolines. Preferably substituted phenols are used, most preferably phenol itself.

Suitable catalysts for the process according to the invention are known in principle, for example, from EP-A 483 632, EP-A 635 476, U.S Pat. No. 5,478,961, EP-A 635 477, U.S. Pat. No. 5,473,094, EP-A 645 364, EP-A 691 326, EP-A 516 355, U.S. Pat. No. 5,239,105 and U.S. Pat. No. 5,136,077.

The educts phosgene and hydroxy compound are used in molar ratios of from 1:0.5 to 1:8, preferably from 1:1.5 to 1:5, particularly preferably from 1:2 to 1:4. The stoichiometric ratio is in this case 1:2.

The catalysts are generally used as granular material, granules, extrudates, rods, balls, shaped bodies having large surface areas, such as hollow extrudates in the form of Raschig rings, hollow cylinders, stars, cartwheels or as fragments. The diameters and lengths of these particles are from 0.5 to 10 mm. They are arranged in the reactor in the form of simple beds.

Suitable reactors for the process according to the invention are known to the person skilled in the art. Examples are tubular reactors, optionally equipped with a cooling or heating jacket, which contain the catalyst in the form of a bed, or tray reactors, wherein the catalyst is distributed as an even layer on several trays located one above the other.

Phosgene and aromatic hydroxy compound may be passed through the reactor in concurrent or countercurrent flow in order to effect the reaction. In vertical reactors, the liquid phase may be passed through the reactor both from the top downwards and from the bottom upwards.

The reaction of phosgene and aromatic hydroxy compound is carried out at temperatures of about 100 to 250° C., preferably from 120 to 230° C., particularly preferably from 130 to 220° C. The heat of reaction is dissipated by vaporising the educts and products to the extent that the temperature of the reaction mixture rises by 50° C. at most, preferably 40° C. at most, particularly preferably not more than 35° C., above the inlet temperature of the reactants.

The pressure varies within the range of from 0.3 to 10 bar, preferably from 0.5 to 7 bar, particularly preferably from 0.8 to 6 bar.

The waste gas formed during the reaction is passed in concurrent or countercurrent flow through a reactor filled with heterogeneous catalyst together with a molten stream of the hydroxy compound, which may also contain chloroformic ester in quantities of <50 wt. %, preferably of <30 wt. %, particularly preferably of <10 wt. %, with residual phosgene and smaller quantities of chloroformic ester possibly still entrained being withdrawn from the gas stream. The liquid mixture leaving the waste gas reactor, after degassing, is adjusted to the required molar ratio by the addition of phosgene and if necessary additional hydroxy compound, heated to the required temperature and passed to the reactor.

The gas stream issuing from the top of the waste gas reactor after the degassing of the reaction mixture consists substantially of hydrogen chloride. Any traces of phosgene still present can be hydrolysed by known methods using a small amount of water in an activated-carbon tower. The quantity of hydroxy compound still present in the stream of hydrogen chloride corresponds to the vapour pressure of the former at the temperature prevailing in the degassing apparatus; it is removed by freezing in a cryogenic trap and can be returned to the reactor. Any residual quantity present is distilled off as aqueous mixture by azeotropic distillation in the subsequent adiabatic absorption of the hydrogen chloride in water and, after recovery, may be passed into the reactor or used for other purposes, such as the production of phenol resins.

The residual quantities of phosgene still present in the hydrogen chloride may also, after the adiabatic absorption with water, where they are expelled with the azeotrope consisting of hydroxy compound and water, advantageously be passed into the activated-carbon tower together with the residual traces of inert gas originating from the educt stream and may be hydrolysed there.

After the reaction mixture has been degassed, an initial crude product is obtained which generally consists predominantly of diaryl carbonate and/or aromatic hydroxy compound and still contains certain quantities of chloroformic ester, which usually amounts to <50 wt. %, preferably <30 wt. %, most preferably <15 wt. %.

This mixture can be supplied directly for working up by distillation and be divided into streams consisting of chloroformic ester and hydroxy compound, of a diaryl carbonate and small quantities of high-boiling components. However, for simplicity and to achieve a more economic distillation process, a reaction mixture which contains no chloroformic ester, or only very small quantities thereof, is more suitable.

For this reason it is more advantageous to introduce the initial crude product, after degassing, into a second reactor containing a heterogeneous catalyst and there the chloroformic ester still present is caused to react with hydroxy compound still present in the mixture or added, under conditions similar to those in the first reactor.

In this process the pressure may be within narrower limits of 0.6 to 6 bar, preferably 0.8 to 4 bar, and the temperature may be somewhat higher, namely from 120 to 250° C., preferably from 140 to 240° C., particularly preferably from 160 to 230° C.

The rate of loading the reactors, measured in kilograms of educt mixture per litre of catalyst volume per hour, depends upon the reaction temperature, the activity of the catalysts and the required conversion. The loading rate is from 0.01 to 20, preferably from 0.02 to 10, particularly preferably from 0.05 to 4 and, most preferably, from 0.1 to 3 kg/1h.

The gas leaving the second reactor is also degassed and the stream of waste gas is likewise passed to the waste gas reactor. The degassed mixture, which contains only small quantities (<3 wt. %, preferably <2 wt. %, particularly preferably <1 wt. %) of chloroformic ester, is freed in a first distillation column from excess hydroxy compound and chloroformic ester, which are removed as overhead product, and, according to demand, passed into the reactor, second reactor or into the waste gas reactor, and reacted further.

The mixture flowing off at the bottom of this column is separated in a second column into residual low-boiling components, which are returned to the upper part of the first column, into pure diaryl carbonate, which is removed laterally from the vapour stream of this second column, and into a mixture of diaryl carbonate and high-boiling components, which leave the column as bottoms Traces of high-boiling components are separated (bottoms) in a third column for the ultimate purification of the dipheyl carbonate, which is removed from this third column as overhead product.

In a fourth distillation device, which is operated continuously of batchwise, the combined bottoms from the second and third columns are separated into bottoms containing the high-boiling components and into diaryl carbonate, which is passed into the lower part of the second column and there purified further.

The comparatively small quantities of bottoms, amounting to <3%, preferably <2%, particularly preferably <1%, of the reaction product, are expediently burnt or used for the production of phenol resin.

EXAMPLES

Continuous production of diphenyl carbonate by phosgenation of phenol in the presence of γ-aluminium oxide and return of the waste gas to an additional reactor

EXAMPLE 1

The apparatus employed for carrying out the process according to the invention and the material flows are shown diagrammatically in FIG. 1.

28.0 parts by weight of phenol 12 from a heated tank I via heat exchanger III (60° C.), together with phenol 14 drawn from the top of the distillation column X and phenol 18 returned from the cryogenic trap XVI, are delivered at standard pressure from above into a waste gas reactor VII which is filled with 150 parts by volume of γ-aluminium oxide and preheated to 170° C. In concurrent flow thereto, the stream of waste gas 15 (weight ratio of phenol/phosgene/ hydrogen chloride/carbon dioxide: 2.9/8.9/87.6/0.6) from the degassing apparatus VI and IX is fed into reactor VII.

The product 11' issuing at the foot of the reactor, which contains phenol, phenyl chloroformate, diphenyl carbonate and by-products in the ratio 95.6/0.01/4.3/0.08, is separated by the degasifier XV into waste gas 16 (weight ratio of phenol/phosgene/hydrogen chloride/carbon dioxide: 3.7/1.3/94.4/0.6) and bottoms 11 (weight ratio of phenol/phenyl chloroformate/diphenyl carbonate and by-products: 95.6/0.01/4.4/0.08).

Phosgene 3, preheated by heat exchanger IV (170° C.), at a rate of 15.05 parts by weight/h, is passed in concurrent flow together with 11 into a reactor V filled with 150 parts by volume of γ-aluminium oxide and preheated to 170° C.

The product 5 issuing at the foot of the reactor, which contains phenol, phenyl chloroformate, diphenyl carbonate and by-products in the ratio 34.3/0.2/65.1/0.4, is separated by the degasifier VI into waste gas 6 (weight ratio of phenol/phosgene/hydrogen chloride/carbon dioxide: 1.5/9.0/88.9/0.6) and bottoms 7 (weight ratio of phenol/phenyl chloroformate/diphenyl carbonate and by-products: 34.0/0.2/65.4/0.4).

The phenyl chloroformate present in the bottoms 7 is converted to diphenyl carbonate at 180° C. by a subsequent reaction with phenol present (if necessary, after addition of further phenol (1' or 14')) in a second reactor VIII, likewise filled with γ-aluminium oxide (150 parts by volume).

The product 8 withdrawn at the foot of the reactor (weight ratio of phenol, diphenyl carbonate and by-products: 33.9/65.7/0.4) is separated by the degasifier IX into waste gas 9 (phenol/hydrogen chloride) and bottoms 10 (weight ratio of phenol, diphenyl carbonate and by-products: 33.7/65.9/0.4).

The streams of waste gas 6 and 9 are combined to form the stream 15 and passed into waste gas reactor VII in concurrent flow with phenol (12, 14 and 18), as described above.

The waste gas 16 issuing at the top of the degasifier XV is supplied to a cryogenic trap XVI, wherein the phenol 18 present (0.43 parts by weight/h) is removed and returned to the waste gas reactor VII.

The waste gas 17 issuing from the cryogenic trap XVI is supplied to a hydrogen chloride absorption unit XVII.

By charging an 18% hydrochloric acid 19 at a rate of 64.2 parts by weight/h, a 30% hydrochloric acid 20 at a rate of 75.1 parts by weight/h is obtained, which can be supplied for electrolysis. The chlorine obtained from the electrolysis can be used again for the production of phosgene.

Traces of entrained phenol may be removed as an azeotrope with water 29.

A destruction plant (activated-carbon tower containing water) can be attached for the decomposition of traces of phosgene still present in the waste gas 30.

The bottoms 10 are passed into a first distillation column X and, at about 80° C./12 mm, are separated into 16.1 parts by weight/h of phenol and bottoms 22 (weight ratio of phenol, diphenyl carbonate and by-products: 0.3/99.1/0.6).

The bottoms 22 are passed into a second distillation column XI, wherein phenol 21 still present (0.1 parts by weight/h) are removed at the top and returned to the upper part of the first column X.

Through a lateral outlet from the gas space of the second column XI, 31.7 parts by weight/h of product 23 (weight ratio of diphenyl carbonate/by-products: 99.9/0.1) is obtained which, in a third distillation column XII, is separated into overhead product 28 (31.7 parts by weight/h of diphenyl carbonate), corresponding to a selectivity of 99.6%, referred to phenol, and bottoms 27.

The product 25 (weight ratio of diphenyl carbonate/by-products: 91.1/8.9) withdrawn at the foot of the distillation column XI, together with 27, are separated in a fourth distillation column XIII at 170° C./12 mm into overhead product 24 (1.4 parts by weight/h of diphenyl carbonate), which is returned into the lower part of the second column XI and the bottoms 26 (high-boiling by-products).

EXAMPLE 2

Carrying out the process according to the invention as described in Example 1, with a charge of 20.10 parts by weight/h of phenol 12 via heat exchanger III into waste gas reactor VII and introduction of preheated phosgene 3 at a rate of 10.69 parts by weight/h via heat exchanger IV into reactor V, results in a phosgene-free stream of waste gas 16, with the selectivity for diphenyl carbonate being unchanged. The following additional variations in the described procedure, which depend on the compositions of educt and product, loading rates of catalyst and temperature, may be mentioned:

a) Dosing of phenol 4 directly into reactor V instead of via waste gas reactor VII at the start of the process.

b) Addition of phenol (1' or 14') as additional reaction partner for the post-reaction in the case of higher concentrations of phenyl chloroformate.

c) Operation without the post-reaction in the reactor VIII, whereby phenyl chloroformate then still present is distilled off in the first distillation column X as low-boiling component 14 together with phenol and fed into-the waste gas reactor VII, or, in an operation without waste gas reactor, is returned to the first reactor V (13).

d) Liquid phase and phosgene are passed in countercurrent flow through reactor V. In this process phosgene from the storage tank II via heat exchanger IV enters from below into the reactor V, and the liquid phase enters from above. For the discharge of the waste gas, the upper part of reactor V is additionally connected with the waste gas reactor VII.

We claim:

1. A process for the continuous production of diaryl carbonates by the reaction of phosgene with aromatic hydroxy compounds in the presence of heterogeneous catalysts, characterised in that 1) a mixture of an aromatic hydroxy compound and optionally chloroformic ester thereof together with phosgene are passed into a reactor filled with heterogeneous catalyst and reacted therein in such a way that the heat of reaction is dissipated by evaporation of the educts and products and thus the reaction temperature rises by 50° C. at most above the inlet temperature of the reaction mixture, 2) the product leaving the reactor is degassed, the waste gas together with a molten stream of the aromatic hydroxy compound, which optionally contains some chloroformic ester, is passed into an additional waste gas reactor filled with heterogeneous catalyst and is reacted therein so that phosgene and optionally chloroformic ester are removed from the stream of waste gas, 3) the reaction product removed from the reactor and degassed is-either led away directly for working up or is fed into a second reactor, wherein residual chloroformic ester is reacted further over a heterogeneous catalyst with aromatic hydroxy compound still present or introduced, to form diaryl carbonate, 4) the product leaving the second reactor is again degassed and this waste gas is passed into the waste gas reactor referred to in 2) with molten aromatic hydroxy compound, 5) the degassed product from the second reactor is fed into a distillation column, aromatic hydroxy compound and traces of chloroformic ester possibly still present are distilled off at the top and are reintroduced into the waste gas reactor or into the first reactor, 6) the bottoms of this first column are passed into a second distillation column, traces of low-boiling components possibly still present are removed from the diaryl carbonate at the top and are reintroduced into the upper part of the first column, 7) diaryl carbonate, possibly containing traces of high-boiling components, is removed from the gas space of the second column, 8) this product is passed into a third column and, by separating the residual quantities of high-boiling components as bottoms, pure diphenyl carbonate is obtained as overhead product, 9) the combined bottoms of the second and third column are passed into a fourth distillation unit, diaryl carbonate is distilled off at the top, is returned to the second column and the high-boiling components are removed from the bottoms of the fourth distillation unit.

* * * * *

UNITED STATES PATENT AND TRADEMARK OFFICE
CERTIFICATE OF CORRECTION

PATENT NO. : 5,900,501
DATED       : May 4, 1999
INVENTOR(S) : Pieter Ooms et al.

It is certified that error appears in the above-indentified patent and that said Letters Patent is hereby corrected as shown below:

Column 2, line 51, "5,478,961" should read --5,473,961--.

Column 4, line 36, "dipheyl" should read -- diphenyl --;
line 39, "of" should -- or --; and
line 60, "weight" should read -- weight/h --.

Signed and Sealed this

Twenty-third Day of November, 1999

Attest:

Q. TODD DICKINSON

*Attesting Officer*            *Acting Commissioner of Patents and Trademarks*